US010472636B2

(12) United States Patent
Lee et al.

(10) Patent No.: US 10,472,636 B2
(45) Date of Patent: Nov. 12, 2019

(54) MUTANT MICROORGANISM PRODUCING L-ASPARTIC ACID DERIVATIVES, AND METHOD FOR PRODUCING L-ASPARTIC ACID DERIVATIVES USING SAME

(71) Applicant: Korea Advanced Institute of Science and Technology, Daejeon (KR)

(72) Inventors: Sang Yup Lee, Daejeon (KR); Tong Un Chae, Daejeon (KR); Chan Woo Song, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 253 days.

(21) Appl. No.: 15/556,458

(22) PCT Filed: Mar. 17, 2016

(86) PCT No.: PCT/KR2016/002736
§ 371 (c)(1),
(2) Date: Sep. 7, 2017

(87) PCT Pub. No.: WO2016/153221
PCT Pub. Date: Sep. 29, 2016

(65) Prior Publication Data
US 2018/0051291 A1 Feb. 22, 2018

(30) Foreign Application Priority Data
Mar. 20, 2015 (KR) .................. 10-2015-0039071

(51) Int. Cl.
| | |
|---|---|
| C12N 1/20 | (2006.01) |
| C12N 15/52 | (2006.01) |
| C12N 9/88 | (2006.01) |
| C12N 15/63 | (2006.01) |
| C12P 7/40 | (2006.01) |
| C12N 15/01 | (2006.01) |
| C12P 7/42 | (2006.01) |
| C12P 13/00 | (2006.01) |
| C12P 13/04 | (2006.01) |
| C12P 13/06 | (2006.01) |
| C12R 1/00 | (2006.01) |

(52) U.S. Cl.
CPC .............. *C12N 15/52* (2013.01); *C12N 1/20* (2013.01); *C12N 9/88* (2013.01); *C12N 15/01* (2013.01); *C12N 15/63* (2013.01); *C12P 7/40* (2013.01); *C12P 7/42* (2013.01); *C12P 13/001* (2013.01); *C12P 13/005* (2013.01); *C12P 13/04* (2013.01); *C12P 13/06* (2013.01); *C12R 1/00* (2013.01)

(58) Field of Classification Search
CPC ............. C12N 1/20; C12N 15/52; C12N 9/88
See application file for complete search history.

(56) References Cited

FOREIGN PATENT DOCUMENTS

| | | |
|---|---|---|
| EP | 0127940 A2 | 12/1984 |
| EP | 0307247 A2 | 3/1989 |
| WO | 9108291 A2 | 6/1991 |
| WO | 2005118719 A2 | 12/2005 |

OTHER PUBLICATIONS

Guest, J.,, et al., "Cloning of the Aspartase Gene (aspA) of *Escherichia coil*", "Journal of General Microbiology", 1984, pp. 1271-1278, vol. 130, No. 5.
Datsenko, K., et al., "One-step Inactivation of Chromosomal Genes in *Escherichia coil* K-12 Using PCR Products", "Proc. Natl. Acad. Sci. USA (PNAS)", Jun. 6, 2000, pp. 6640-6645, vol. 97, No. 12.
Ikai, H., et al., "Two Genes Involved in the 1,3-Diaminopropane Production Pathway in Haemophilus influenzae", "Biological and Pharmaceutical Bulletin", Feb. 1998, pp. 170-179, vol. 21, No. 2.
Konst, P. M., et al., "Stabilized and Immobilized Bacillus subtilis Arginase for the Biobased Production of Nitrogen- Containing Chemicals", "Advanced Synthesis & Catalysis", Jun. 8, 2010, pp. 1493-1502, vol. 352.
Lee, P. C., et al., "Batch and continuous cultivation of Anaerobiospirillum succiniciproducens for the production of succinic acid from whey", "Applied Microbiology and Biotechnology", 2000, pp. 23-27, vol. 54.
Lee, P. C., et al., "Succinic Acid Production with Reduced By-Product Formation in the Fermentation of Anaerobiospirillum succiniciproducens Using Glycerol as a Carbon Source", "Biotechnology and Bioengineering", Jan. 5, 2001, pp. 41-48, vol. 72, No. 1.
Lee, P. C., et al., "Isolation and characterization of a new succinic acid-producing bacterium, Mannheimia succiniciproducens MBEL55E, from bovine rumen", "Applied Microbiology and Biotechnology", Feb. 8, 2002, pp. 663-668, vol. 58.
Lee, P., et al., "Biological conversion of wood hydrolysate to succinic acid by Anaerobiospirillum succiniciproducens", "Biotechnol. Lett.", Jan. 2003, pp. 111-114, vol. 25, No. 2.
Lee, P. C., et al., "Batch and continuous cultures of Mannheimia succiniciproducens MBEL55E for the production of succinic acid from whey and corn steep liquor", "Bioprocess and Biosystems Engineering", Oct. 6, 2003, pp. 63-67, vol. 26.

(Continued)

*Primary Examiner* — Tekchand Saidha
(74) *Attorney, Agent, or Firm* — Hultquist, PLLC; Steven J. Hultquist

(57) ABSTRACT

The present invention relates to a mutant organism having the ability to produce aspartic acid derivatives, wherein a gene encoding the glyoxylate shunt regulator and a gene encoding fumarase are deleted and a gene encoding aspartase is overexpressed compared to that in a wild-type strain, and to a method for producing L-aspartic acid derivatives using the same. According to the present invention, various aspartic acid derivatives, including L-alanine, 3-aminopropionic acid, threonine, 1,3-diaminopropane, lysine, methionine, 3-hydroxypropionic acid, cadaverine, 5-aminovaleric acid, etc., can be produced by biological methods.

17 Claims, 5 Drawing Sheets
(3 of 5 Drawing Sheet(s) Filed in Color)
Specification includes a Sequence Listing.

(56) References Cited

OTHER PUBLICATIONS

Papierz, M., et al., "Selection and Activation of *Escherichia coli* Strains for L-aspartic Acid Biosynthesis", "Polish Journal of Microbiology", 2007, pp. 71-76, vol. 56, No. 2.
Park, J. H., et al., "Metabolic pathways and fermentative production of L-aspartate family amino acids", "Biotechnology Journal", 2010, pp. 560-577, vol. 5.
Salerno, C., et al., "Kinetics of Coupled Reactions Catalyzed by Aspartate Aminotransferase and Glutamate Dehydrogenase", "European Journal of Biochemistry", 1982, pp. 511-517, vol. 121.
Song, C. W., et al., "Metabolic Engineering of *Escherichia coli* for the Production of Fumaric Acid", "Biotechnology and Bioengineering", Jul. 2013, pp. 2025-2034, vol. 110, No. 7.
Suzuki, Y., et al, "Production of L-Aspartic Acid from Fumaric Acid by a Fumaric Acid-Assimilating Obligate Thermophile, Bacillus stearothermophilus KP 1041*", "European Journal of Applied Microbiology and Biotechnology", 1980, pp. 23-27, vol. 11.
Note: For the non-patent literature citations that no month of publication is indicated, the year of publication is more than 1 year prior to the effective filing date of the present application.

SEQUENCE LISTING

```
<160> NUMBER OF SEQ ID NOS: 26

<210> SEQ ID NO 1
<211> LENGTH: 70
<212> TYPE: DNA
<213> ORGANISM: Artificial Sequence
<220> FEATURE:
<223> OTHER INFORMATION: primer

<400> SEQUENCE: 1
agaaaacccg ccgttgccac cgcaccagcg actggacagg ttcagtcttt gacactatag      60
aacgcggccg                                                             70

<210> SEQ ID NO 2
<211> LENGTH: 70
<212> TYPE: DNA
<213> ORGANISM: Artificial Sequence
<220> FEATURE:
<223> OTHER INFORMATION: primer

<400> SEQUENCE: 2
tcgccgcttt aatcaccatc gcgccaaact cggtcacgcg gtcatcggta ccgcataggc      60
cactagtgga                                                             70

<210> SEQ ID NO 3
<211> LENGTH: 70
<212> TYPE: DNA
<213> ORGANISM: Artificial Sequence
<220> FEATURE:
<223> OTHER INFORMATION: primer

<400> SEQUENCE: 3
gttgtctgaa gagaaagcga gcgccattcg tcaggcggcg gatgaagtac gacactatag      60
aacgcggccg                                                             70

<210> SEQ ID NO 4
<211> LENGTH: 70
<212> TYPE: DNA
<213> ORGANISM: Artificial Sequence
<220> FEATURE:
<223> OTHER INFORMATION: primer

<400> SEQUENCE: 4
attggacgga agacgttcag ttcaaagtta ccggaagcgc cccccatgtt ccgcataggc      60
cactagtgga                                                             70
```

```
<210> SEQ ID NO 5
<211> LENGTH: 70
<212> TYPE: DNA
<213> ORGANISM: Artificial Sequence
<220> FEATURE:
<223> OTHER INFORMATION: primer

<400> SEQUENCE: 5
tgatactgag tattacctgc taaccagcga acacgttagc gtatctgaat gacactatag    60
aacgcggccg                                                           70

<210> SEQ ID NO 6
<211> LENGTH: 70
<212> TYPE: DNA
<213> ORGANISM: Artificial Sequence
<220> FEATURE:
<223> OTHER INFORMATION: primer

<400> SEQUENCE: 6
acgccgggaa atcttccact tcaattttcc agatggcttc cattcccagt ccgcataggc    60
cactagtgga                                                           70

<210> SEQ ID NO 7
<211> LENGTH: 70
<212> TYPE: DNA
<213> ORGANISM: Artificial Sequence
<220> FEATURE:
<223> OTHER INFORMATION: primer

<400> SEQUENCE: 7
gcacgccatt ttcgaataac aaatacagag ttacaggctg gaagctatgt gacactatag    60
aacgcggccg                                                           70

<210> SEQ ID NO 8
<211> LENGTH: 70
<212> TYPE: DNA
<213> ORGANISM: Artificial Sequence
<220> FEATURE:
<223> OTHER INFORMATION: primer

<400> SEQUENCE: 8
cgcattttct cgacgaggaa gtttttcagt ttgccgggag tcagcagggc ccgcataggc    60
cactagtgga                                                           70

<210> SEQ ID NO 9
<211> LENGTH: 70
<212> TYPE: DNA
<213> ORGANISM: Artificial Sequence
<220> FEATURE:
<223> OTHER INFORMATION: primer

<400> SEQUENCE: 9
cctgtacacg gcgaggctct cccccttgc cacgcgtgag aacgtaaaaa gacactatag     60
aacgcggccg                                                           70

<210> SEQ ID NO 10
<211> LENGTH: 70
<212> TYPE: DNA
<213> ORGANISM: Artificial Sequence
<220> FEATURE:
<223> OTHER INFORMATION: primer

<400> SEQUENCE: 10
```

```
gagagaaggt ctggattgca gaaccaatcg gcggccaaat gaaggacagc ccgcataggc    60
cactagtgga                                                           70

<210> SEQ ID NO 11
<211> LENGTH: 70
<212> TYPE: DNA
<213> ORGANISM: Artificial Sequence
<220> FEATURE:
<223> OTHER INFORMATION: primer

<400> SEQUENCE: 11
cgatgtcgca gagtatgccg gtgtctctta tcagaccgtt tcccgcgtgg gacactatag    60
aacgcggccg                                                           70

<210> SEQ ID NO 12
<211> LENGTH: 70
<212> TYPE: DNA
<213> ORGANISM: Artificial Sequence
<220> FEATURE:
<223> OTHER INFORMATION: primer

<400> SEQUENCE: 12
ccagtgagac gggcaacagc tgattgccct tcaccgcctg gccctgagag ccgcataggc    60
cactagtgga                                                           70

<210> SEQ ID NO 13
<211> LENGTH: 70
<212> TYPE: DNA
<213> ORGANISM: Artificial Sequence
<220> FEATURE:
<223> OTHER INFORMATION: primer

<400> SEQUENCE: 13
ggtaaccagc gcaaaggttt ctcctgtaat agcagccggt taaccccggc gacactatag    60
aacgcggccg                                                           70

<210> SEQ ID NO 14
<211> LENGTH: 72
<212> TYPE: DNA
<213> ORGANISM: Artificial Sequence
<220> FEATURE:
<223> OTHER INFORMATION: primer

<400> SEQUENCE: 14
ggaacttccc tggtacccaa cagatcttct tcgatacgaa tgttgtttga catggtctgt    60
ttcctgtgtg aa                                                        72

<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
agacaggaat tcatgctgcg caccatcctc g                                   31

<210> SEQ ID NO 16
<211> LENGTH: 37
<212> TYPE: DNA
<213> ORGANISM: Artificial Sequence
<220> FEATURE:
<223> OTHER INFORMATION: primer
```

<400> SEQUENCE: 16
agacaggagc tcctaaatgc ttctcgacgt caaaagc                             37

<210> SEQ ID NO 17
<211> LENGTH: 31
<212> TYPE: DNA
<213> ORGANISM: Artificial Sequence
<220> FEATURE:
<223> OTHER INFORMATION: primer

<400> SEQUENCE: 17
agacaggaat tcatgctgcg caccatcctc g                                   31

<210> SEQ ID NO 18
<211> LENGTH: 37
<212> TYPE: DNA
<213> ORGANISM: Artificial Sequence
<220> FEATURE:
<223> OTHER INFORMATION: primer

<400> SEQUENCE: 18
agacaggagc tcctaaatgc ttctcgacgt caaaagc                             37

<210> SEQ ID NO 19
<211> LENGTH: 56
<212> TYPE: DNA
<213> ORGANISM: Artificial Sequence
<220> FEATURE:
<223> OTHER INFORMATION: primer

<400> SEQUENCE: 19
agacaggagc tcacaggaaa cagaccatgg aacataaaac tttatcaata ggtttc        56

<210> SEQ ID NO 20
<211> LENGTH: 47
<212> TYPE: DNA
<213> ORGANISM: Artificial Sequence
<220> FEATURE:
<223> OTHER INFORMATION: primer

<400> SEQUENCE: 20
agacagtcta gattacccccc ttatatattt tttatatagt acttgtg                 47

<210> SEQ ID NO 21
<211> LENGTH: 33
<212> TYPE: DNA
<213> ORGANISM: Artificial Sequence
<220> FEATURE:
<223> OTHER INFORMATION: primer

<400> SEQUENCE: 21
agacagtcta gagaaagccc gaggatcgaa cga                                 33

<210> SEQ ID NO 22
<211> LENGTH: 33
<212> TYPE: DNA
<213> ORGANISM: Artificial Sequence
<220> FEATURE:
<223> OTHER INFORMATION: primer

<400> SEQUENCE: 22
agacagcctg caggtcaggc gatgccgttg agc                                 33

<210> SEQ ID NO 23

```
<211> LENGTH: 31
<212> TYPE: DNA
<213> ORGANISM: Artificial Sequence
<220> FEATURE:
<223> OTHER INFORMATION: primer

<400> SEQUENCE: 23
agacaggaat tcatgtcggt tacatctgtc a                              31

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
agacagggta ccttacgcgc cccg                                      24

<210> SEQ ID NO 25
<211> LENGTH: 31
<212> TYPE: DNA
<213> ORGANISM: Artificial Sequence
<220> FEATURE:
<223> OTHER INFORMATION: primer

<400> SEQUENCE: 25
agacagggta cctttcacac aggaaacaga c                              31

<210> SEQ ID NO 26
<211> LENGTH: 32
<212> TYPE: DNA
<213> ORGANISM: Artificial Sequence
<220> FEATURE:
<223> OTHER INFORMATION: primer

<400> SEQUENCE: 26
agacagctgc agttagtcta tgggcggcac gt                             32
```

MUTANT MICROORGANISM PRODUCING L-ASPARTIC ACID DERIVATIVES, AND METHOD FOR PRODUCING L-ASPARTIC ACID DERIVATIVES USING SAME

CROSS-REFERENCE TO RELATED APPLICATIONS

This application is a U.S. national phase under the provisions of 35 U.S.C. § 371 of International Patent Application No. PCT/KR2016/002736 filed Mar. 17, 2016, which in turn claims priority of Korean Patent Application No. 10-2015-0039071 filed Mar. 20, 2015. The disclosures of such international patent application and Korean priority patent application are hereby incorporated herein by reference in their respective entireties, for all purposes.

TECHNICAL FIELD

The present invention relates to a mutant organism having the ability to produce aspartic acid derivatives, wherein a gene encoding the glyoxylate shunt regulator and a gene encoding fumarase are deleted, and a gene encoding aspartase is overexpressed compared to that in a wild-type strain, and to a method for producing L-aspartic acid derivatives using the same.

BACKGROUND ART

Industrial production of L-aspartic acid is performed by an enzymatic conversion method using aspartase that uses fumaric acid and ammonia as substrates. L-aspartic acid is highly useful by itself, and can also be converted into various useful chemical derivatives, including L-alanine, 3-aminopropionic acid, acrylic acid, 1,3-diaminopropane, threonine, lysine, methionine, 3-hydroxypropionic acid, cadaverine, 5-aminovaleric acid and the like, by biological methods.

In conventional metabolic engineering methods for improving strains, L-aspartic acid derivatives were produced through a pathway that produces L-aspartic acid from oxaloacetate by use of aspartate aminotransferase. However, in this pathway, the process of producing L-aspartic acid from oxaloacetate involves a reaction that converts glutamic acid to α-ketoglutaric acid, and this reaction was coupled with an NAD(P)H consuming reaction that reproduces L-glutamic acid from α-ketoglutaric acid (Salerno et al., Eur. J. Biochem., 121:511, 1982). Due to such characteristics, the enzymatic reaction that uses aspartate aminotransferase is complicated to use as a major pathway for producing a desired chemical substance, and additionally requires reducing power. Thus, it appears that this enzymatic reaction is less efficient than an aspartase reaction which requires no reducing power and in which ammonia reacts directly with fumaric acid to produce L-aspartic acid.

Accordingly, the present inventors have developed a strain having the ability to produce fumaric acid that is an L-aspartic acid precursor, and have found that, if the expression level of aspartase in the strain is increased to thereby construct a mutant microorganism that uses the aspartase pathway as a major pathway for producing L-aspartic acid, the mutant microorganism can efficiently produce 3-aminopropionic acid (beta alanine), 3-hydroxypropionic acid and 1,3-diaminopropane, which are L-aspartic acid derivatives, thereby completing the present invention.

DISCLOSURE OF INVENTION

Technical Problem

It is an object of the present invention to provide a mutant microorganism that uses the aspartase pathway as a major pathway for producing L-aspartic acid.

Technical Solution

To achieve the above object, the present invention provides a mutant microorganism having the ability to produce L-aspartic acid derivatives, in which a gene encoding the glyoxylate shunt regulator and a gene encoding fumarase are deleted, and a gene encoding aspartase is overexpressed compared to that in a wild-type strain.

The present invention also provides a method for producing L-aspartic acid derivatives, the method comprising the steps of: producing L-aspartic acid derivatives by culturing the above described mutant microorganism in a medium containing a carbon source; and recovering the produced L-aspartic acid derivatives.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

In the present invention, a strain having the ability to produce fumaric acid was constructed. Furthermore, aspartase in the strain was overexpressed, thereby establishing a new metabolic pathway that can efficiently convert sugar into L-aspartic acid. In addition, a method of producing L-aspartic acid derivatives from L-aspartic acid by a biological method was developed.

Therefore, in one aspect, the present invention is directed to a mutant microorganism having the ability to produce L-aspartic acid from sugar, wherein a gene encoding the glyoxylate shunt regulator and a gene encoding fumarase are deleted, and a gene encoding aspartase is overexpressed compared to that in a wild-type strain.

In the present invention, the local regulator gene that regulates the metabolic flux to the glyoxylate shunt was deleted, and the gene having fumarase activity was deleted. Then, the gene having aspartase activity was overexpressed, thereby establishing a system that can produce L-aspartic acid derivatives from sugar by using a reaction catalyzed by aspartase as a major pathway for producing L-aspartic acid.

In the present invention, methods for increasing aspartase activity comprise replacing the native promoter of aspA gene on the genome with the strong promoter trc, tac, T7, lac, trp or the like, and transforming a strain by cloning an aspartase-encoding gene into an expression vector.

In the present invention, the microorganism may be selected from the group consisting of bacteria, yeasts, and fungi. Preferably, the bacteria may be selected from the group consisting of *Corynebacterium* sp., and *E. coli*, and may more preferably be *E. coli*.

In the present invention, the sugar may be selected from the group consisting of monosaccharides, disaccharides and polysaccharides, comprising glucose, sucrose, galactose, lactose, maltose, xylose, glycerol, fructose and sugar cane, which are carbon sources usable by microorganisms.

In the present invention, the gene encoding the glyoxylate shunt local regulator may be an iclR gene, the gene encoding fumarase may be fumA, fumB or fumC, and the gene encoding aspartase may be an aspA gene.

Figure 1:
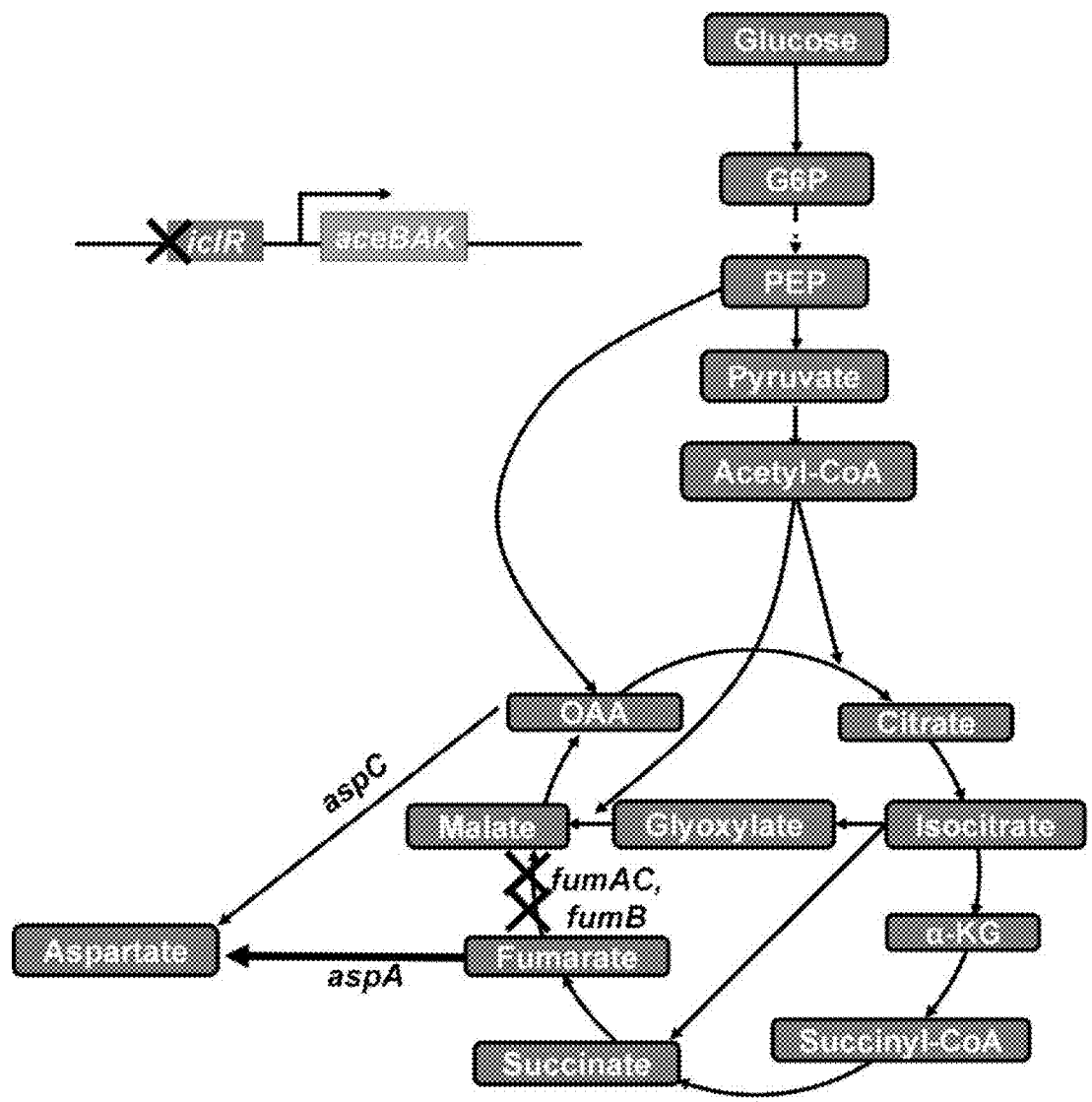
FIG. 1 shows a method for constructing a metabolic pathway of a mutant microorganism that uses an aspartase pathway as a major metabolic pathway to convert glucose into L-aspartic acid.

The process of producing L-aspartic acid derivatives using the mutant microorganism according to the present invention is characterized in that fumaric acid converted from glucose is converted into L-aspartic acid by high aspartase activity, and then the L-aspartic acid is converted into L-aspartic acid derivatives by an additionally introduced gene for synthesis of L-aspartic acid derivatives (FIG. 1).

In an example of the present invention, in order to construct a mutant microorganism that can produce 3-aminopropionic acid, 3-hydroxypropionic acid and 1,3-diaminopropane by using a reaction catalyzed by aspartase as a major pathway for producing L-aspartic acid derivatives, the iclR (glyoxylate shunt local regulator) gene and the known fumarase genes fumA, fumB and fumC were deleted from *E. coli* W3110, and the ptsG (phosphotransferase system) gene was deleted for the purpose of reducing the production of by-products, and the lacI gene was additionally deleted for construction of a constitutive expression system. In addition, the promoter of the aspA gene on the genome was replaced with a strong trc promoter. As a result, a mutant microorganism that can efficiently produce L-aspartic acid from glucose by aspartase activity could be constructed. In addition, aspartate-α-decarboxylase was introduced to thereby construct a strain that can produce 3-aminopropionic acid from glucose, and 2-ketoglutarate 4-aminotransferase and L-2,4-diaminobutyrate decarboxylase were introduced to thereby construct a strain capable of producing 1,3-diaminopropane (FIG. 2).

Figure 2:
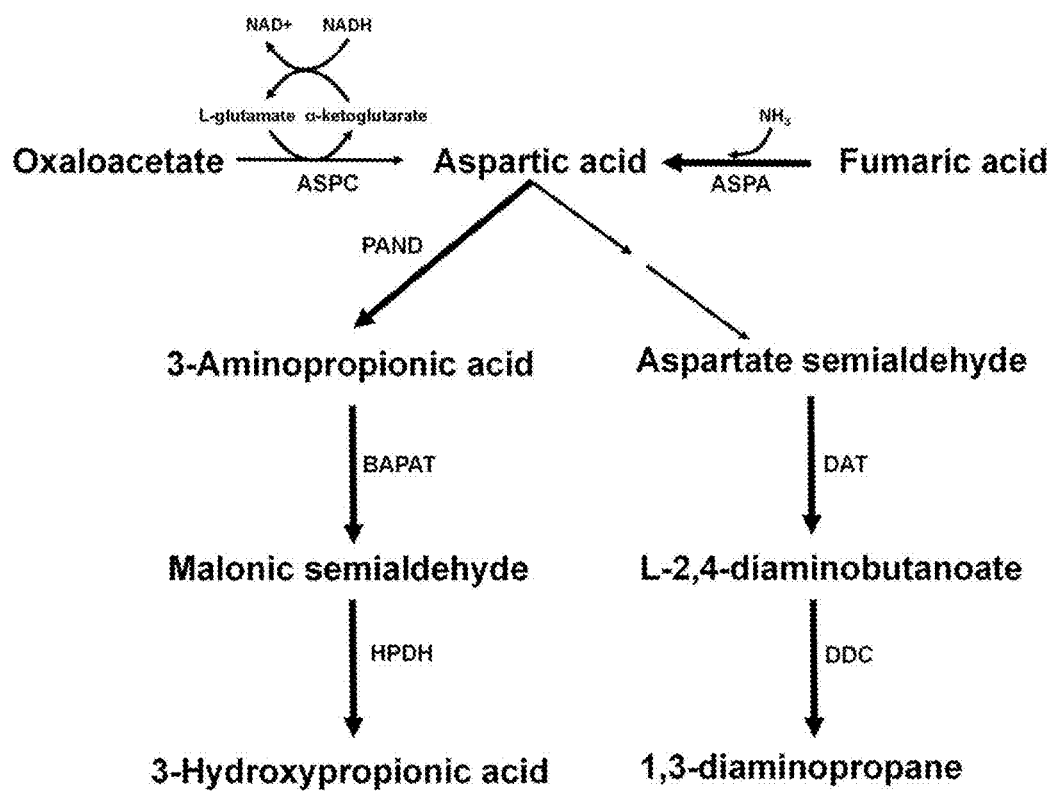
FIG. 2 compares the aspartase pathway for producing 3-aminopropionic acid, 3-hydroxypropionic acid and 1,3-diaminopropane, which are L-aspartic acid derivatives, according to an embodiment of the present invention, with the aspartate transaminase pathway.

Furthermore, beta-alanine pyruvate transaminase and 3-hydroxypropionate/3-hydroxyisobutyrate dehydrogenase or malonic semialdehyde reductase were introduced into the strain capable of producing 3-aminopropionic acid, thereby constructing a strain capable of producing 3-hydroxypropionic acid from glucose (FIG. 2).

In another aspect, the present invention is directed to a method for producing L-aspartic acid derivatives, the method comprising the steps of: producing L-aspartic acid derivatives by culturing the above-described mutant microorganism in a sugar-containing medium; and recovering the produced L-aspartic acid derivatives.

As used herein, the term "L-aspartic acid derivatives" refers to a collection of chemical substances that can be converted from L-aspartic acid by biological pathways, and the term is intended to include all chemical substances that can be converted from L-aspartic acid by enzymatic reactions in vivo.

Examples of representative L-aspartic acid derivatives comprise threonine, methionine, lysine, L-alanine, isoleucine, and the like, and may comprise 3-aminopropionic acid, acrylic acid, 1,3-diaminopropane, cadaverine, 5-aminovaleric acid, 3-hydroxypropionic acid, and the like, each of which can be used as a polymer precursor.

Therefore, the L-aspartic acid derivatives may be selected from the group consisting of threonine, methionine, lysine, L-alanine, isoleucine, 3-aminopropionic acid, acrylic acid, 1,3-diaminopropane, cadaverine, 3-hydroxypropionic acid, and 5-aminovaleric acid, but are not limited thereto.

In an example of the present invention, only a mutant microorganism, which produces L-aspartic acid derivatives (3-aminopropionic acid, 3-hydroxypropionic acid and 1,3-diaminopropane) by culture, was constructed by way of example. However, the present invention encompasses producing various L-aspartic acid derivatives in addition to the above-mentioned chemical substances by supplying L-aspartic acid from sugar by the aspartase pathway and converting the L-aspartic acid to various L-aspartic acid derivatives by biological processes.

In an example of the present invention, only a certain medium and a certain culture method were illustrated. However, as reported in the literature (Lee et al., Bioprocess Biosyst. Eng., 26:63, 2003; Lee et al., Appl. Microbiol. Biotechnol., 58:663, 2002; Lee et al., Biotechnol. Lett., 25:111, 2003; Lee et al., Appl. Microbiol. Biotechnol., 54:23, 2000; Lee et al., Biotechnol. Bioeng., 72:41, 2001), the use of saccharification liquid such as whey or CSL (corn steep liquor), and other medium, or the use of various culture methods such as fed-batch culture or continuous culture, will also be obvious to a person having ordinary skill in the art.

In still another aspect, the present invention is directed to a mutant microorganism having the ability to produce 3-aminopropionic acid from sugar, wherein a iclR gene and a gene encoding fumarase are deleted, a aspA gene is overexpressed compared to that in a wild-type strain, and a gene encoding aspartate dehydroxylase is introduced and to a method for producing 3-aminopropionic acid, the method comprising the steps of: producing 3-aminopropionic acid by culturing the above-described mutant microorganism in a medium containing a carbon source; and recovering the produced 3-aminopropionic acid.

In an example of the present invention, it could be seen that 3-aminopropionic acid was not produced in wild-type *E. coli* W3110. Furthermore, it could be seen that, in *E. coli* W3110 introduced with an pTac15k panD expression vector as a control, 0.3 g/L of 3-aminopropionic acid was produced, but in a strain of the present invention, obtained by deleting the iclR gene, the fumA, fumB, fumC and ptsG (phosphotransferase system) genes and the lacI gene from *E. coli* W3110, replacing the promoter of aspA gene with a strong trc promoter and introducing a pTac15k panD expression vector into the strain, 0.85 g/L of 3-aminopropionic acid was produced. The above results suggest that a strain, which has the ability to produce fumaric acid and which uses the aspartase pathway as a major pathway for producing L-aspartic acid, is more effective in production of 3-aminopropionic acid, which is an L-aspartic acid derivative, compared to a wild-type strain and a strain that does not use a reaction catalyzed by aspartase as a major pathway for producing L-aspartic acid.

In yet another aspect, the present invention is directed to a mutant microorganism having the ability to produce 1,3-diaminopropane from sugar, wherein a iclR gene and a gene encoding fumarase are deleted, a aspA gene is overexpressed compared to that in a wild-type strain, and genes encoding 2-ketoglutarate 4-aminotransferase and L-2,4-diaminobutyrate decarboxylase are introduced and to a method for producing 1,3-diaminopropane, the method comprising the steps of: producing 1,3-diaminopropane by culturing the above-described mutant microorganism in a medium containing a carbon source; and recovering the produced 1,3-diaminopropane.

In an example of the present invention, it could be seen that 1,3-diaminopropane was not produced in wild-type E. coli W3110. Furthermore, it could be seen that, in E. coli W3110 introduced with a p15COdatddc expression vector as a control, 0.21 g/L of 1,3-diaminopropane was produced, but in a strain of the present invention, obtained by deleting the iclR gene, the fumA, fumB, fumC and ptsG (phosphotransferase system) genes and the lacI gene from E. coli W3110, replacing the promoter of aspA gene with a strong trc promoter and introducing a p15COdatddc expression vector into the strain, 0.39 g/L of 1,3-diaminopropane was produced.

In a further aspect, the present invention is directed to a mutant microorganism having the ability to produce 3-hydroxypropionic acid from sugar, wherein a iclR gene and a gene encoding fumarase are deleted, a aspA gene is overexpressed compared to that in a wild-type strain, and wherein a gene encoding aspartate dehydroxylase, a gene encoding beta alanine pyruvate transaminase, and a gene encoding 3-hydroxypropionate/3-hydroxyisobutyrate dehydrogenase or malonic semialdehyde reductase, are introduced and to a method for producing 3-hydroxypropionic acid, the method comprising the steps of: producing 3-hydroxypropionic acid by culturing the above-described mutant microorganism in a medium containing a carbon source; and recovering the produced 3-hydroxypropionic acid.

In an example of the present invention, it could be seen that 3-hydroxyproionic acid was not produced in wild-type E. coli W3110. Furthermore, it could be seen that, in E. coli W3110 introduced with a p100-99ApanDbce4042pae0132 expression vector as a control, 0.08 g/L of 3-hydroxyproionic acid was produced, but in a strain of the present invention, obtained by deleting the iclR gene, the fumA, fumB, fumC and ptsG (phosphotransferase system) genes and the lacI gene from E. coli W3110, replacing the promoter of aspA gene with a strong trc promoter and introducing a p100-99ApanDbce4042pae0132 expression vector into the strain, 0.2 g/L of 3-hydroxyproionic acid was produced.

The above results suggest that a strain, which has the ability to produce fumaric acid and which uses the aspartase pathway as a major pathway for producing L-aspartic acid, is more effective in production of 3-hydroxyproionic acid, which is an L-aspartic acid derivative, compared to a wild-type strain.

As used herein, the term "deletion" means mutating, substituting or deleting a portion or the whole of the nucleotide sequence of the gene of interest so that the gene of interest will not be expressed or will not exhibit enzymatic activity even when being expressed, and the term also encompasses blocking biosynthesis pathways in which an enzyme encoded by the gene of interest is involved.

As used herein, the term "overexpression" refers to the expression of the gene of interest in cells at levels higher than the expression level of the gene under normal conditions, and is intended to include increasing expression levels either by replacing the promoter of a gene on the genome with a strong promoter or by cloning the gene of interest into an expression vector and transforming cells with the expression vector.

As used herein, the term "vector" means a DNA construct containing a DNA sequence operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the present invention is intended to include other types of vectors with the same function as that would be known or known in the art. Typical expression vectors for mammalian cell culture expression are based on, for example, pRK5 (EP 307,247), pSV16B (WO91/08291), and pVL1392 (Pharmingen).

As used herein, the term "expression control sequence" refers to the DNA sequences essential for the expression of the coding sequence operably linked in a particular host organism. Such control sequences include a promoter for performing transcription, any operator sequence for controlling such transcription, a sequence for encoding a suitable mRNA ribosomal binding site, and a sequence for controlling the termination of transcription and translation. For example, control sequences suitable for prokaryotes include a promoter, an arbitrary operator sequence, and a ribosomal binding site. Eukaryotic cells include promoters, polyadenylation signals, and enhancers. The factor having the greatest effect on the expression level of the gene in the plasmid is a promoter. SRα promoter, cytomegalovirus promoter and the like are preferably used as a promoter for high expression.

To express the DNA sequence of the present invention, any of a wide variety of expression control sequences may be used in the vector. Examples of useful expression control sequences include, for example, the early and late promoters of SV40 or adenovirus, the lac system, the trp system, the TAC or TRC system, T3 and T7 promoters, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast α-mating system, and other sequences known to control the expression of genes of prokaryotic or eukaryotic cells or their viruses, and various combinations thereof. T7 RNA polymerase promoter Φ10 may be effectively used to express the protein NSP in E. coli.

A nucleic acid sequence is operably linked when it is placed in a functional relationship with another nucleic acid sequence. The nucleotide sequence may be a gene and a control sequence(s) linked to be capable of expressing the gene when it binds to a control sequence(s) (e.g., transcription-activating protein). For example, DNA for a pre-sequence or a secretory leader is operably linked to DNA encoding polypeptide when expressed as pre-protein participating in secretion of polypeptide; a promoter or an enhancer is operably linked to a coding sequence when affecting the transcription of the sequence; and a ribosome-binding site is operably linked to a coding sequence when affecting the transcription of the sequence, or to a coding sequence when arranged to facilitate translation. Generally, the term "operably linked" means that the DNA linked sequences are contiguous, and in the case of the secretory leader, are contiguous and present in a reading frame. However, an enhancer is not necessarily contiguous. The linkage between these sequences is performed by ligation at a convenient restriction enzyme site. However, when the site does not exist, a synthetic oligonucleotide adaptor or a linker is used according to a conventional method.

The term "expression vector" as used herein generally means a double-stranded DNA fragment functioning as a recombinant carrier into which a heterologous DNA fragment is inserted. Here, the heterologous DNA means a hetero-type DNA, which is not naturally found in a host cell. The expression vector may be self-replicable regardless of host chromosomal DNA once in a host cell, and may produce several copies of the vector and (heterologous) DNA inserted thereinto.

As is well known in the art, in order to increase the expression level of a transfected gene in a host cell, a corresponding gene should be operably linked to transcription and translation expression control sequences which are operated in a selected expression host. Preferably, the expression control sequences and the corresponding gene are included in one expression vector together with a bacterial selection marker and a replication origin. When an expression host cell is a eukaryotic cell, an expression vector should further include an expression marker which is useful in a eukaryotic expression host.

The host cell transformed or transfected by the aforementioned expression vector constitutes another aspect of the present invention. As used herein, the term "transformation" means that DNA can be replicated as a factor outside of chromosome or by means of completion of the entire chromosome by introducing DNA into a host. As used herein, the term "transfection" means that an expression vector is accepted by a host cell regardless of whether or not any coding sequence is actually expressed.

Host cells that are used in the present invention may be prokaryotic cells or eukaryotic cells. In addition, a host is generally used, into which DNA is introduced with high efficiency and in which the introduced DNA is expressed with high efficiency. Examples of host cells that may be used in the present invention include known prokaryotic and eukaryotic hosts such as *E. coli*, *Pseudomonas* spp., *Bacillus* spp., *Streptomyces* spp., fungi or yeast, insect cells such as *Spodoptera frugiperda* (SF9), animal cells such as CHO and mouse cells, African green monkey cells such as COS 1, COS 7, BSC 1, BSC 40 and BMT 10, and tissue-cultured human cells. In the present invention, when cDNA encoding the NSP protein is to be cloned, animal cells are preferably used as a host. When COS cells are used, a plasmid with SV40 replication origin can be present as multiple copies of an episome in the cells and can be expressed at higher levels than a conventional level, because the COS cell express SV40 large T antigen. The introduced DNA sequence may be obtained from the same species as the host cells, or may be of species different from the host cells, or may be a hybrid DNA sequence comprising any heterogeneous or homologous DNA.

Of course, it should be understood that all vectors and expression control sequences do not equally function to express DNA sequences according to the present invention. Similarly, all hosts do not equally function with respect to the same expression system. However, one skilled in the art may appropriately select from among various vectors, expression control sequences, and hosts without either departing from the scope of the present invention or bearing excessive experimental burden. For example, a vector must be selected considering a host cell, because the vector must be replicated in the host cell. Specifically, the copy number of the vector, the ability of regulating the copy number and the expression of other protein encoded by the corresponding vector (e.g., the expression of an antibiotic marker) should also be considered. Also, an expression control sequence may be selected taking several factors into consideration. For example, relative strength, control capacity and compatibility with the DNA sequence of the present invention of the sequence should be deliberated particularly with respect to possible secondary structures. Further, the selection of a unicellular host cell may be made under consideration of compatibility with a selected vector, toxicity of a product encoded by a DNA sequence, secretory nature of the product, ability to correctly fold a polypeptide, fermentation or cultivation requirements, ability to ensure easy purification of a product encoded by a DNA sequence, or the like. Within the scope of these parameters, one of ordinary skill in the art may select various vectors/expression control sequences/host combinations that can express the DNA sequences of the invention in either large scale animal culture or fermentation. In cloning the cDNA of an NSP protein by the expression cloning strategy, screening procedures such as a binding method, a panning method, and a film emulsion method can be used.

In the definition of the present invention, the term "substantially pure" means that a polypeptide according to the present invention and the DNA sequences encoding the polypeptide substantially do not contain any other proteins derived from bacteria.

As host cells for expressing recombinant proteins, procaryotic cells, such as *E. coli* and *Bacillus* subtillis, which can be cultured at a high concentration within a short time, easily genetically modified and have well established genetic and physiological properties, have been widely used. However, to solve various problems, including the post-translational modification, secretion, three-dimensional active structure and activation of proteins, a wide range from microorganisms to higher organisms, including unicellular eukaryotic cells, yeasts (*Pichia pastoris, Saccharomyces cerevisiae, Hansenula polymorpha*, etc.), filamentous fungi, insect cells, plant cells, and mammalian cells, has recently been used as host cells for recombinant protein production. Thus, it will be obvious to one skilled in the art to use not only *E. coli* cells illustrated in Examples, but also other host cells.

EXAMPLES

Hereinafter, the present invention will be described in further detail with reference to examples. It will be obvious to a person having ordinary skill in the art that these examples are for illustrative purposes only and are not to be construed to limit the scope of the present invention. Thus, the substantial scope of the present invention will be defined by the appended claims and equivalents thereof.

Particularly, although *E. coli* W3110 was used as a host microorganism in the following examples, it will be obvious to a person skilled in the art that other *E. coli* species, or bacteria, yeast or fungi, may also be used. In addition, although the following examples illustrated only a gene, derived from a specific strain, as the gene to be introduced, it will be obvious to a person skilled in the art that the kind of gene to be introduced is not limited as long as it can be expressed in host cells and can exhibit the same activity as the illustrated gene.

Example 1

1-1: Deletion of iclR Gene (Construction of W3110-I)

From *E. coli* W3110 (ATTC 39936), the iclR gene was deleted by a one-step inactivation method (Warner et al., PNAS, 6; 97(12): 6640-6645, 2000) using primers of SEQ ID NOs: 1 and 2, and antibiotic resistance was removed.

[SEQ ID NO: 1]
iclR k/o F:
5-AGAAAACCCGCCGTTGCCACCGCACCAGCGACTGGACAGGTTCAGTCT

TTGACACTATAGAACGCGGCCG-3

[SEQ ID NO: 2]
iclR k/o R:
5-TCGCCGCTTTAATCACCATCGCGCCAAACTCGGTCACGCGGTCATCGG

TACCGCATAGGCCACTAGTGGA-3

1-2: Deletion of fumC Gene (Construction of W3110-IC)

From *E. coli* W3110-I constructed in Example 1-1, the fumC gene was deleted by a one-step inactivation method using primers of SEQ ID NOs: 3 and 4, and antibiotic resistance was removed.

[SEQ ID NO: 3]
fumC k/o F:
5-GTTGTCTGAAGAGAAAGCGAGCGCCATTCGTCAGGCGGCGGATGAAGT

ACGACACTATAGAACGCGGCCG-3

[SEQ ID NO: 4]
fumC k/o R:
5-ATTGGACGGAAGACGTTCAGTTCAAAGTTACCGGAAGCGCCCCCCATG

TTCCGCATAGGCCACTAGTGGA-3

1-3: Deletion of fumA Gene (Construction of W3110-ICA)

From *E. coli* W3110-IC constructed in Example 1-2, the fumA gene was deleted by a one-step inactivation method using primers of SEQ ID NOs: 5 and 6, and antibiotic resistance was removed.

[SEQ ID NO: 5]
fumA k/o F:
5-TGATACTGAGTATTACCTGCTAACCAGCGAACACGTTAGCGTATCTGA

ATGACACTATAGAACGCGGCCG-3

[SEQ ID NO: 6]
fumA k/o R:
5-ACGCCGGGAAATCTTCCACTTCAATTTTCCAGATGGCTTCCATTCCCA

GTCCGCATAGGCCACTAGTGGA-3

1-4: Deletion of fumB Gene (Construction of W3110-ICAB)

From *E. coli* W3110-ICA constructed in Example 1-3, the fumB gene was deleted by a one-step inactivation method using primers of SEQ ID NOs: 7 and 8, and antibiotic resistance was removed.

[SEQ ID NO: 7]
fumB k/o F:
5-GCACGCCATTTTCGAATAACAAATACAGAGTTACAGGCTGGAAGCTAT

GTGACACTATAGAACGCGGCCG-3

[SEQ ID NO: 8]
fumB k/o R:
5-CGCATTTTCTCGACGAGGAAGTTTTTCAGTTTGCCGGGAGTCAGCAGG

GCCCGCATAGGCCACTAGTGGA-3

1-5: Deletion of ptsG Gene (Construction of W3110-ICABP)

From *E. coli* W3110-ICAB constructed in Example 1-4, the ptsG gene was deleted by a one-step inactivation method using primers of SEQ ID NOs: 9 and 10, and antibiotic resistance was removed.

[SEQ ID NO: 9]
ptsG k/o F:
5-CCTGTACACGGCGAGGCTCTCCCCCCTTGCCACGCGTGAGAACGTAAA

AAGACACTATAGAACGCGGCCG-3

[SEQ ID NO: 10]
ptsG k/o R:
5-GAGAGAAGGTCTGGATTGCAGAACCAATCGGCGGCCAAATGAAGGACA

GCCCGCATAGGCCACTAGTGGA-3

1-6: Deletion of lacI Gene (Construction of W3110-ICABPI)

From *E. coli* W3110-ICABP constructed in Example 1-5, the lacI gene was deleted by a one-step inactivation method using primers of SEQ ID NOs: 11 and 12, and antibiotic resistance was removed.

[SEQ ID NO: 11]
lacI k/o F:
5-CGATGTCGCAGAGTATGCCGGTGTCTCTTATCAGACCGTTTCCCGCGT

GGGACACTATAGAACGCGGCCG-3

[SEQ ID NO: 12]
lacI k/o R:
5-CCAGTGAGACGGGCAACAGCTGATTGCCCTTCACCGCCTGGCCCTGAG

AGCCGCATAGGCCACTAGTGGA-3

1-7: Replacement of Native Promoter of aspA Gene with Strong Trc Promoter (Construction of W3110-ICABPI-Apr)

From *E. coli* W3110-ICABPI constructed in Example 1-6, the aspA native promoter was replaced with the strong trc promoter by a one-step inactivation method using primers of SEQ ID NOs: 13 and 14.

[SEQ ID NO: 13]
aspA p/r F:
5-GGTAACCAGCGCAAAGGTTTCTCCTGTAATAGCAGCCGGTTAACCCCG

GCGACACTATAGAACGCGGCCG-3

[SEQ ID NO: 14]
aspA p/r R:
5 GGAACTTCCCTGGTACCCAACAGATCTTCTTCGATACGAATGTTGTTT

GACATGGTCTGTTTCCTGTGTGAA-3

Example 2

2-1: Construction of pTac15k panD Vector for Producing 3-Aminopropionic Acid from L-Aspartic Acid Using the chromosomal DNA of *Corynebacterium glutamicum* (ATCC 13032) as a template, PCR was performed with primers of SEQ ID NOs: 15 and 16, thereby constructing a panD gene fragment encoding aspartate-decarboxylase.

```
                                          [SEQ ID NO: 15]
panD F:
5'-AGACAGGAATTCATGCTGCGCACCATCCTCG-3'

[SEQ ID NO: 16]
panD R:
5'-AGACAGGAGCTCCTAAATGCTTCTCGACGTCAAAAGC-3'
```

Figure 3:
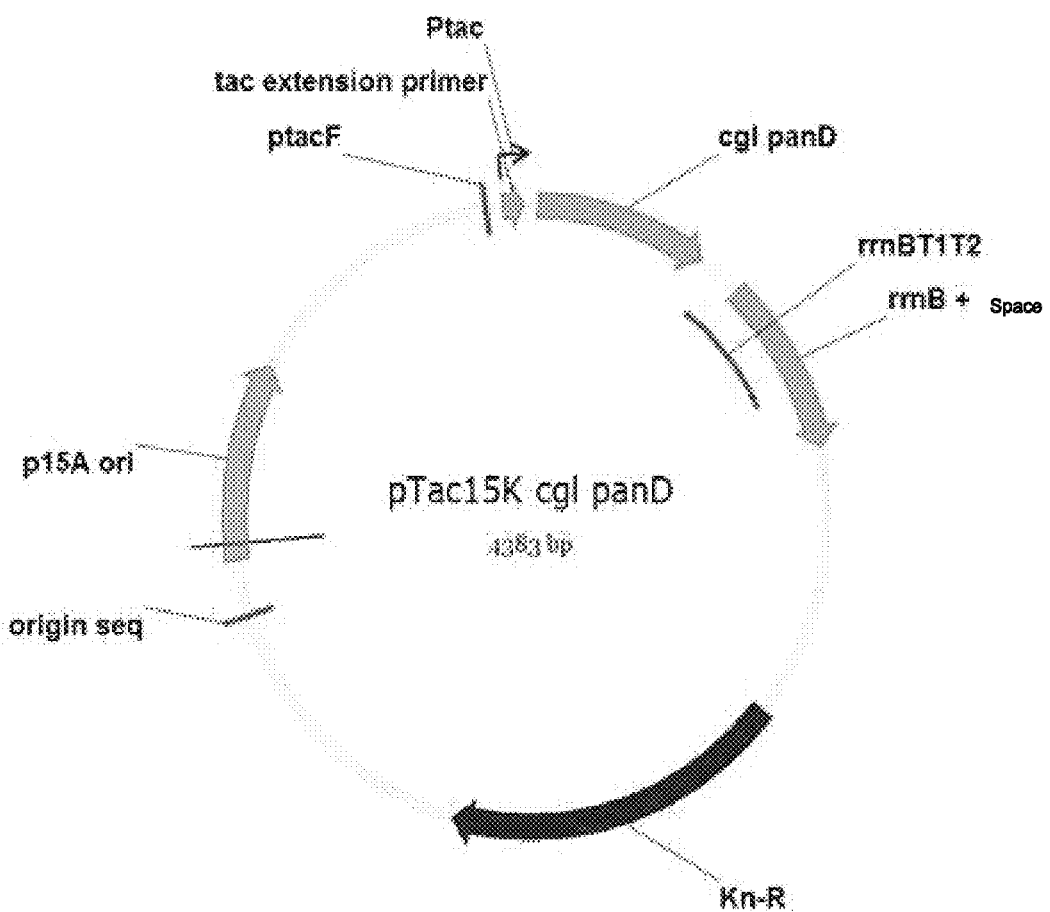
FIG. 3 shows a pTac15 k panD-overexpressing plasmid for producing 3-aminopropionic acid, in which panD gene is inserted.
Figure 4:
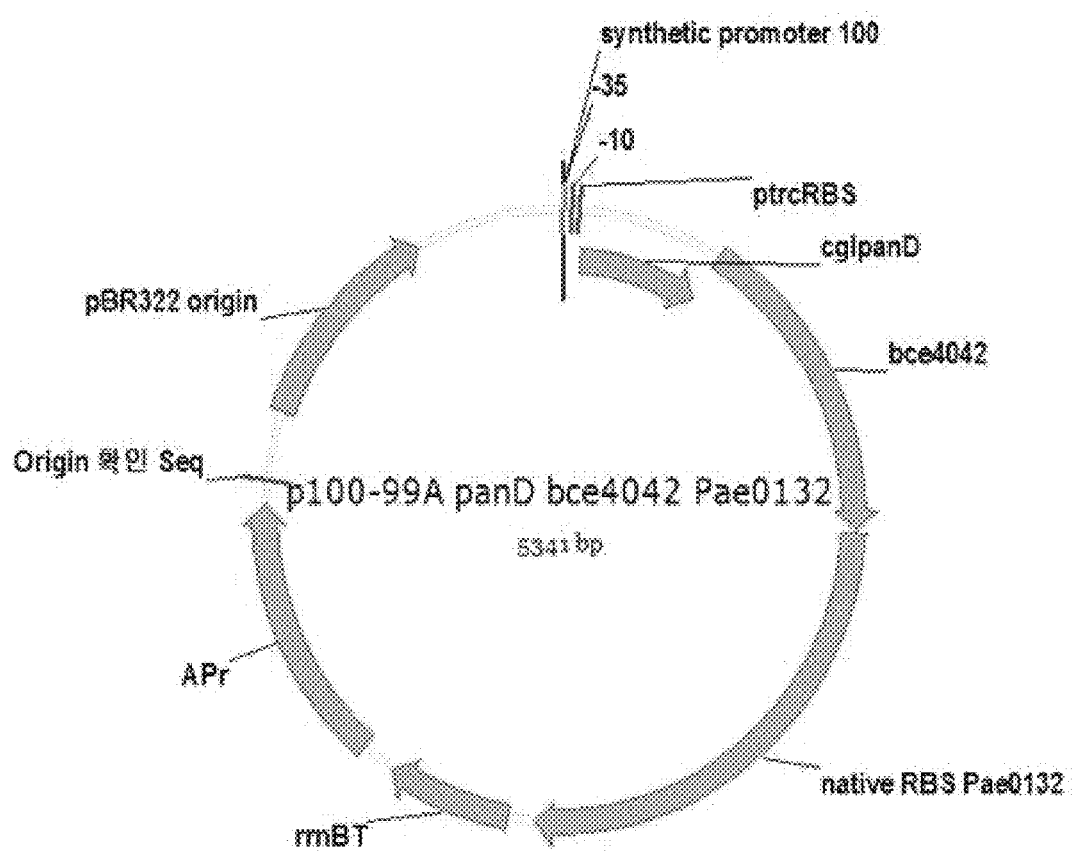
FIG. 4 shows a p100-99ApanDbce4042pae0132-overexpressing plasmid for producing 3-hydroxypropionic acid, in which panD gene, bce4042 gene and pae0132 gene are inserted.
Figure 5:
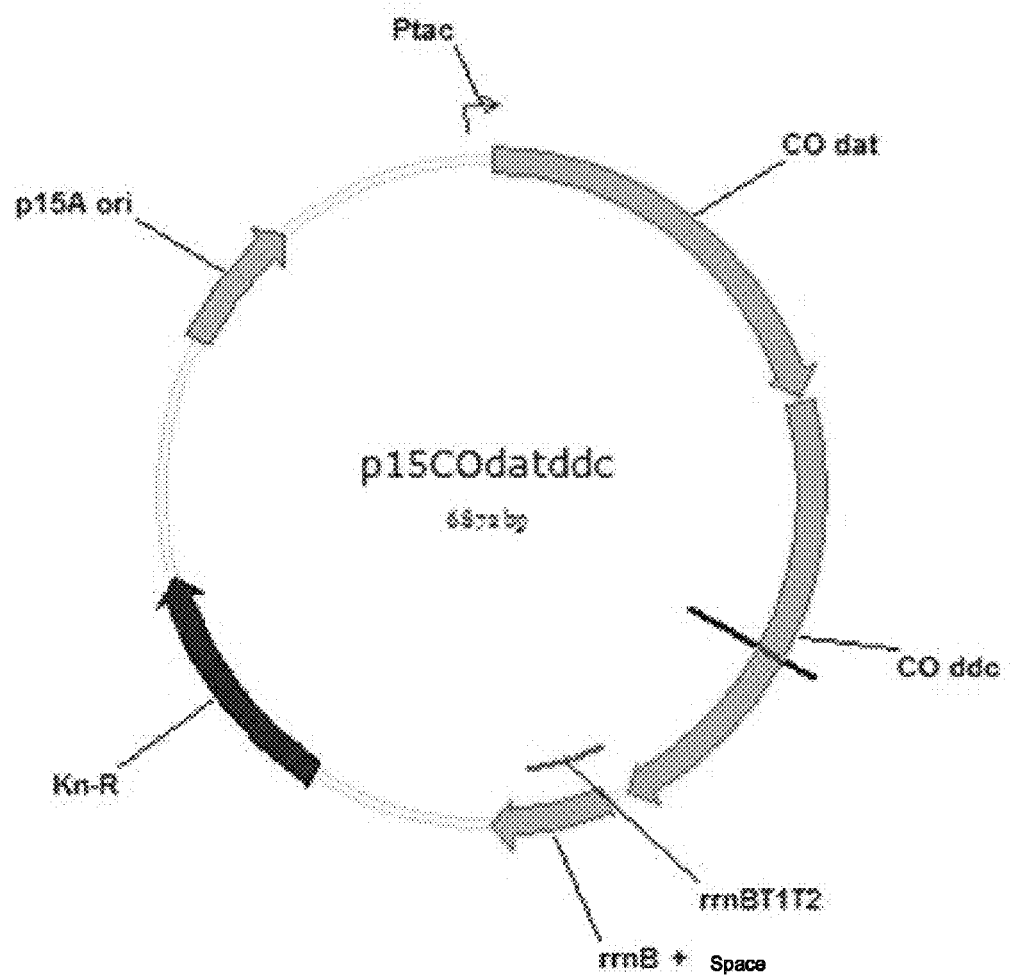
FIG. 5 shows a p15COdatddc-overexpressing plasmid for producing 1,3-diaminopropane, in which dat gene and ddct gene are inserted.

Next, the constructed panD fragment was treated with restriction enzymes (EcoRI and SacI), and then ligated by T4 DNA ligase into a pTac15k plasmid that performs strong gene expression with tac promoter, thereby constructing the recombinant plasmid pTac15k panD (FIG. 3).

2-1: Construction of p100-99A panD Bce4042 Pae0132 Vector for Producing 3-Hydroxypropionic Acid from L-Aspartic Acid Using the chromosomal DNA of *Corynebacterium glutamicum* (ATCC 13032) as a template, PCR was performed with primers of SEQ ID NOs: 17 and 18, thereby constructing a panD gene fragment encoding aspartate-decarboxylase. Using the chromosomal DNA of *Bacillus cereus* (ATCC 14579) as a template, PCR was performed with primers of SEQ ID NOs: 19 and 20, thereby constructing a bce4042 gene fragment encoding 3-hydroxyisobutyrate dehydrogenase. In addition, using the chromosomal DNA of *Pseudomonas aeroginosa* PA01 as a template, PCR was performed with primers of SEQ ID NOs: 21 and 22, thereby constructing a pae0132 gene fragment encoding beta alanine pyruvate transaminase.

```
                                          [SEQ ID NO: 17]
panD F:
5'-AGACAGGAATTCATGCTGCGCACCATCCTCG-3'

[SEQ ID NO: 18]
panD R:
5'-AGACAGGAGCTCCTAAATGCTTCTCGACGTCAAAAGC-3'

[SEQ ID NO: 19]
bce4042 F:
5'-AGACAGGAGCTCACAGGAAACAGACCATGGAACATAAAACTTTATCA
ATAGGTTTC-3'

[SEQ ID NO: 20]
bce4042 R:
5'-AGACAGTCTAGATTACCCCCTTATATATTTTTTATATAGTACTTGT
G-3'

[SEQ ID NO: 21]
pae0132 F:
5'-AGACAGTCTAGAGAAAGCCCGAGGATCGAACGA-3'

[SEQ ID NO: 22]
pae0132 R:
5'-AGACAGCCTGCAGGTCAGGCGATGCCGTTGAGC-3'
```

Next, the constructed panD, bce4042 and pae0132 fragments were treated with restriction enzymes (EcoRI and SacI), (SacI and XbaI) and (XbaI and SbfI), and then ligated by T4 DNA ligase into a p100-99A plasmid that performs gene expression with p100 promoter (ttgacggctagctcagtcctaggtacagtgctagc: SEQ ID NO: 23), thereby constructing the recombinant plasmid p100-99ApanDbce4042pae0132.

2-3: Construction of p15COdatddc Vector for Producing 1,3-Diaminopropane from L-Aspartic Acid Using artificially synthesized *E. coli* codon optimized dat gene as a template, PCR was performed with primers of SEQ ID NOs: 23 and 24, thereby constructing a dat gene fragment encoding 2-ketoglutarate 4-aminotransferase. In addition, using artificially synthesized *E. coli* codon optimized ddc gene as a template, PCR was performed with primers of SEQ ID NOs: 25 and 26, thereby constructing a ddc gene fragment encoding L-2,4-diaminobutanolate decarboxylase.

```
                                          [SEQ ID NO: 23]
COdat F:
5'-AGACAGGAATTCATGTCGGTTACATCTGTCA-3'

[SEQ ID NO: 24]
COdat R:
5'-AGACAGGGTACCTTACGCGCCCCG-3'

[SEQ ID NO: 25]
COddc F:
5'-AGACAGGGTACCTTTCACACAGGAAACAGAC-3'

[SEQ ID NO: 26]
COddc R:
5'-AGACAGCTGCAGTTAGTCTATGGGCGGCACGT-3'
```

Next, the constructed dat and ddc fragments were treated with restriction enzymes (EcoRI DNA KpnI), and (KpnI and PstI), and then ligated by T4 DNA ligase into a pTac15K plasmid that performs gene expression with tac promoter, thereby constructing the recombinant plasmid p15COdatddc.

Example 3: Measurement of 3-Aminopropionic Acid Production Ability in Mutant Microorganism The pTac15k panD plasmid constructed in Example 2-1 was introduced into the strain (constructed in Example 1-7) suitable for producing L-aspartic acid derivatives by the aspartase pathway. As control strains, a strain obtained by introducing pTac15k panD plasmid into the strain of Example 1-6, in which replacement of the promoter of the aspA gene was not performed, and *E. coli* W3110, were used.

Mutant microorganisms having the ability to produce 3-aminopropionic acid were selected on LB plate medium containing 30 μg/ml of kanamycin. The transformed strain was inoculated into 10 ml of LB medium and pre-cultured at 37° C. for 12 hours. Next, 3 ml of the preculture was inoculated and cultured in 50 ml of modified MR medium in a 350-ml flask.

The composition of modified MR medium (pH 6.5) was composed of: per liter of distilled water, 15 g glucose, 9 g $(NH_4)_2SO_4$, 6.67 g $KH_2PO_4$, 4.0 g $(NH_4)_2HPO_4$, 3.0 g yeast extract, 2 g $NaHCO_3$, 0.8 g citric acid, 0.8 g $MgSO_4 7H_2O$, 0.01 g $CaCl_2 2H_2O$, and 5 ml trace metal solution (per liter of distilled water, 10 g $FeSO_4 7H_2O$, 2.2 g $ZnSO_4 4H_2O$, 0.58 g $MnSO_4 4H_2O$, 1 g $CuSO_4 5H_2O$, 0.1 g $(NH_4)_6Mo_7O_{24} 4H_2O$, 0.02 g $Na_2B_4O_7 10H_2O$). Culture was performed in a shaking incubator at 37° C. and 220 rpm for 24 hours. After culture, the culture medium was centrifuged at 10,000 rpm for 10 minutes, and the supernatant was collected and analyzed by liquid chromatography to measure the production of 3-aminopropionic acid.

As a result, as can be seen in Table 1 below, 3-aminopropionic acid was not produced in wild-type E. coli W3110. Furthermore, it could be seen that, in the control strain obtained by introducing the pTac15k panD expression vector into wild-type E. coli W3110, 0.3 g/L of 3-aminopropionic acid was produced, and in the control stain obtained by introducing the pTac15k panD expression vector into the strain of Example 1-6, 3-aminopropionic acid was not produced. However, it could be seen that, in the strain obtained by introducing the pTac15k panD expression vector into the strain of Example 1-7 in which the promoter of aspA gene was replaced with a strong promoter, 0.85 g/L of 3-aminopropionic acid was produced.

The above results suggest that a strain, which has the ability to produce fumaric acid and which uses the aspartase pathway as a major pathway for producing L-aspartic acid, is more effective in production of 3-aminopropionic acid, which is an L-aspartic acid derivative, compared to a wild-type strain and a strain that does not use a reaction catalyzed by aspartase as a major pathway for producing L-aspartic acid.

TABLE 1

3-Aminopropionic Acid Production
(g/L) in Mutant Microorganisms

| Strain | 3-aminopropionic acid |
| --- | --- |
| W3110 | 0 |
| W3110 + pTac15k panD | 0.3 |
| W3110-ICABPI + pTac15k panD | 0 |
| W3110-ICABPI-Apr + pTac15k panD | 0.85 |

Example 4: Measurement of 3-Hydroxypropionic Acid Production Ability in Mutant Microorganism The p100-99ApanDbce4042pae0132 plasmid constructed in Example 2-2 was introduced into the strain (constructed in Example 1-7) suitable for producing L-aspartic acid derivatives by the aspartase pathway. As a control strain, E. coli W3110 introduced with p100-99ApanDbce4042pae0132 plasmid, was used.

Mutant microorganisms having the ability to produce 3-hydroxypropionic acid were selected on LB plate medium containing 50 μg/ml of ampicillin. The transformed strain was inoculated into 10 ml of LB medium and pre-cultured at 37° C. for 12 hours. Next, 3 ml of the preculture was inoculated and cultured in 50 ml of modified MR medium in a 350-ml flask.

The composition of modified MR medium (pH 6.5) was composed of: per liter of distilled water, 15 g glucose, 9 g $(NH_4)_2SO_4$, 6.67 g $KH_2PO_4$, 4.0 g $(NH_4)_2HPO_4$, 3.0 g yeast extract, 2 g $NaHCO_3$, 0.8 g citric acid, 0.8 g $MgSO_4 7H_2O$, 0.01 g $CaCl_2 2H_2O$, and 5 ml trace metal solution (per liter of distilled water, 10 g $FeSO_4 7H_2O$, 2.2 g $ZnSO_4 4H_2O$, 0.58 g $MnSO_4 4H_2O$, 1 g $CuSO_4 5H_2O$, 0.1 g $(NH_4)6Mo_7O_{24} 4H_2O$, 0.02 g $Na_2B_4O_7 10H_2O$). Culture was performed in a shaking incubator at 37° C. and 220 rpm for 24 hours. After culture, the culture medium was centrifuged at 10,000 rpm for 10 minutes, and the supernatant was collected and analyzed by liquid chromatography to measure the production of 3-hydroxypropionic acid.

As a result, as can be seen in Table 2 below, 3-hydroxypropionic acid was not produced in wild-type E. coli W3110. Furthermore, it could be seen that, in the control strain obtained by introducing the p100-99ApanDbce4042pae0132 expression vector into wild-type E. coli W3110, 0.08 g/L of 3-hydroxypropionic acid was produced. However, it could be seen that, in the strain obtained by introducing the p100-99ApanDbce4042pae0132 expression vector into the strain of Example 1-7 in which the promoter of aspA gene was replaced with a strong promoter, 0.2 g/L of 3-hydroxypropionic acid was produced.

The above results suggest that a strain, which has the ability to produce fumaric acid and which uses the aspartase pathway as a major pathway for producing L-aspartic acid, is more effective in production of 3-hydroxypropionic acid, which is an L-aspartic acid derivative, compared to a wild-type strain.

TABLE 2

3-hydroxypropionic acid Production
(g/L) in Mutant Microorganisms

| Strain | 3-hydroxypropionic acid |
| --- | --- |
| W3110 | 0 |
| W3110 + p100-99A panD bce4042 pae0132 | 0.08 |
| W3110-ICABPI-Apr + p100-99A panD bce4042 pae0132 | 0.2 |

Example 5: Measurement of 1,3-Diaminopropane Production Ability in Mutant Microorganism The p15COdatddc plasmid constructed in Example 2-3 was introduced into the strain (constructed in Example 1-7) suitable for producing L-aspartic acid derivatives by the aspartase pathway. As a control strain, E. coli W3110 introduced with p15COdatddc plasmid, was used.

Mutant microorganisms having the ability to produce 1,3-diaminopropane were selected on LB plate medium containing 30 μg/ml of kanamycin. The transformed strain was inoculated into 10 ml of LB medium and pre-cultured at 37° C. for 8 hours. Next, 1.5 ml of the preculture was inoculated and cultured in 50 ml of modified MR medium in a 350-ml flask.

The composition of modified MR medium (pH 7.0) was composed of: per liter of distilled water, 10 g glucose, 3 g $(NH_4)_2SO_4$, 6.67 g $KH_2PO_4$, 4.0 g $(NH_4)_2HPO_4$, 3.0 g yeast extract, 2 g $NaHCO_3$, 0.8 g citric acid, 0.8 g $MgSO_4 7H_2O$, 0.01 g $CaCl_2 2H_2O$, and 5 ml trace metal solution (per liter of distilled water, 10 g $FeSO_4 7H_2O$, 2.2 g $ZnSO_4 4H_2O$, 0.58 g $MnSO_4 4H_2O$, 1 g $CuSO_4 5H_2O$, 0.1 g $(NH_4)6Mo_7O_{24} 4H_2O$, 0.02 g $Na_2B_4O_7 10H_2O$). Culture was performed in a shaking incubator at 37° C. and 220 rpm for 36 hours. After culture, the culture medium was centrifuged at 10,000 rpm for 10 minutes, and the supernatant was collected and analyzed by liquid chromatography to measure the production of 1,3-diaminopropane.

As a result, as can be seen in Table 3 below, 1,3-diaminopropane was not produced in wild-type E. coli W3110. Furthermore, it could be seen that, in the control strain obtained by introducing the p15COdatddc expression vector into wild-type E. coli W3110, 0.21 g/L of 1,3-diaminopropane was produced. However, it could be seen that, in the strain obtained by introducing the p15COdatddc expression vector into the strain of Example 1-7 in which the promoter of aspA gene was replaced with a strong promoter, 0.39 g/L of 1,3-diaminopropane was produced.

The above results suggest that a strain, which has the ability to produce fumaric acid and which uses the aspartase pathway as a major pathway for producing L-aspartic acid, is more effective in production of 1,3-diaminopropane, which is an L-aspartic acid derivative, compared to a wild-type strain.

TABLE 3

| 1,3-diaminopropane Production (g/L) in Mutant Microorganisms | |
|---|---|
| Strain | 1,3-diaminopropane |
| WL3110 | 0 |
| WL3110 + p15COdatddc | 0.21 |
| W3110-ICABPI-Apr + p15COdatddc | 0.39 |

INDUSTRIAL APPLICABILITY

According to the present invention, various aspartic acid derivatives, including L-alanine, 3-aminopropionic acid, 1,3-diaminopropane, acrylic acid, threonine, lysine, methionine, 3-hydroxypropionic acid, cadaverine, 5-aminovaleric acid, etc., can be produced from carbon sources such as glucose, sucrose, galactose, lactose, maltose, glycerol, fructose and the like by biological methods.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A mutant microorganism having the ability to produce L-aspartic acid derivatives from sugar, wherein a gene encoding the glyoxylate shunt regulator and a gene encoding fumarase are deleted, and a gene encoding aspartase is overexpressed compared to that in a wild-type strain.

2. The mutant microorganism of claim 1, wherein the overexpression of the gene encoding aspartase is performed by introducing a vector comprising the gene encoding aspartase or replacing a wild-type promoter with a strong promoter in the chromosome of the host strain.

3. The mutant microorganism of claim 1, wherein the microorganism is selected from the group consisting of bacteria, yeasts, and fungi.

4. The mutant microorganism of claim 1, wherein the gene encoding the glyoxylate shunt regulator is an iclR gene.

5. The mutant microorganism of claim 1, wherein the gene encoding fumarase is selected from the group consisting of fumA, fumB and fumC.

6. The mutant microorganism of claim 1, wherein the gene encoding aspartase is an aspA gene.

7. The mutant microorganism of claim 1, wherein the strong promoter is selected from the group consisting of a trc promoter, a tac promoter, a T7 promoter, an lac promoter, and a trp promoter.

8. The mutant microorganism of claim 1, wherein the L-aspartic acid derivatives are selected from the group consisting of threonine, methionine, lysine, L-alanine, isoleucine, acrylic acid, 3-aminopropionic acid, 1,3-diaminopropane, cadaverine, 3-hydroxypropionic acid, and 5-aminovaleric acid.

9. The mutant microorganism of claim 1, wherein the sugar is selected from the group consisting of glucose, sucrose, galactose, maltose, xylose, glycerol, fructose and sugar cane, which are carbon sources usable by microorganisms.

10. A method for producing L-aspartic acid derivatives, the method comprising the steps of:
producing L-aspartic acid derivatives by culturing the mutant microorganism of claim 1 in a medium containing a carbon source; and
recovering the produced L-aspartic acid derivatives.

11. The method of claim 10, wherein the L-aspartic acid derivatives are selected from the group consisting of threonine, methionine, lysine, L-alanine, isoleucine, acrylic acid, 3-aminopropionic acid, 1,3-diaminopropane, cadaverine, 3-hydroxypropionic acid, and 5-aminovaleric acid.

12. A mutant microorganism having the ability to produce 3-aminopropionic acid from sugar, wherein a iclR gene and a gene encoding fumarase are deleted, a aspA gene is overexpressed compared to that in a wild-type strain, and a gene encoding aspartate dehydroxylase is introduced.

13. A mutant microorganism having the ability to produce 1,3-diaminopropane from sugar, wherein a ic1R gene and a gene encoding fumarase are deleted, a aspA gene is overexpressed compared to that in a wild-type strain, and genes encoding 2-ketoglutarate 4-aminotransferase and L-2,4-diaminobutyrate decarboxylase are introduced.

14. A mutant microorganism having the ability to produce 3-hydroxypropionic acid from sugar, wherein a ic1R gene and a gene encoding fumarase are deleted, a aspA gene is overexpressed compared to that in a wild-type strain, and a gene encoding aspartate dehydroxylase, a gene encoding 3-hydroxypropionate/3-hydroxyisobutyrate dehydrogenase or malonic semialdehyde reductase, and a gene encoding beta alanine pyruvate transaminase, are introduced.

15. A method for producing 3-aminopropionic acid, the method comprising the steps of:
    producing 3-aminopropionic acid by culturing the mutant microorganism of claim 12 in a medium containing a carbon source; and
    recovering the produced 3-aminopropionic acid.

16. A method for producing 1,3-diaminopropane, the method comprising the steps of:
    producing 1,3-diaminopropane by culturing the mutant microorganism of claim 13 in a medium containing a carbon source; and
    recovering the produced 1,3-diaminopropane.

17. A method for producing 3-hydroxypropionic acid, the method comprising the steps of:
    producing 3-hydroxypropionic acid by culturing the mutant microorganism of claim 14 in a medium containing a carbon source; and
    recovering the produced 3-hydroxypropionic acid.

* * * * *

UNITED STATES PATENT AND TRADEMARK OFFICE
CERTIFICATE OF CORRECTION

PATENT NO. : 10,472,636 B2
APPLICATION NO. : 15/556458
DATED : November 12, 2019
INVENTOR(S) : Lee et al.

It is certified that error appears in the above-identified patent and that said Letters Patent is hereby corrected as shown below:

In the Specification

Column 12, Line 31: "EcoRI DNA KpnI" should be -- EcoRI and KpnI --.

Signed and Sealed this
Fourteenth Day of January, 2020

Andrei Iancu
*Director of the United States Patent and Trademark Office*